(12) United States Patent
Tanaka

(10) Patent No.: US 7,217,942 B2
(45) Date of Patent: May 15, 2007

(54) PLASMA LEAK MONITORING METHOD, PLASMA PROCESSING APPARATUS AND PLASMA PROCESSING METHOD

(75) Inventor: Hideki Tanaka, Yamanashi (JP)

(73) Assignee: Tokyo Electron Limited (JP)

( * ) Notice: Subject to any disclaimer, the term of this patent is extended or adjusted under 35 U.S.C. 154(b) by 699 days.

(21) Appl. No.: 10/644,745

(22) Filed: Aug. 21, 2003

(65) Prior Publication Data
US 2005/0277209 A1 Dec. 15, 2005

(30) Foreign Application Priority Data
Aug. 22, 2002 (JP) .............................. 2002-241454

(51) Int. Cl.
*H01L 21/00* (2006.01)
(52) U.S. Cl. ...................... 250/554; 250/226
(58) Field of Classification Search ................ 250/554, 250/226
See application file for complete search history.

(56) References Cited

U.S. PATENT DOCUMENTS

| | | | | |
|---|---|---|---|---|
| 6,791,692 | B2* | 9/2004 | Powell et al. ................ | 356/496 |
| 2003/0085662 | A1* | 5/2003 | Kwon et al. ............. | 315/111.21 |
| 2003/0205460 | A1* | 11/2003 | Buda ...................... | 204/192.13 |
| 2004/0168771 | A1* | 9/2004 | Mitrovic ................ | 156/345.46 |

FOREIGN PATENT DOCUMENTS

| | | |
|---|---|---|
| JP | 64-081197 | 3/1989 |
| JP | 2000-100795 | 4/2000 |
| JP | 2001-319922 | 11/2001 |
| WO | WO 00/03421 | 1/2000 |

OTHER PUBLICATIONS

English Abstract of JP 64-081197.
English Abstract of JP 2000-100795.
English Abstract of JP 2001-319922.

* cited by examiner

*Primary Examiner*—John R. Lee
(74) *Attorney, Agent, or Firm*—Finnegan, Henderson, Farabow, Garrett & Dunner, LLP

(57) ABSTRACT

In a plasma processing apparatus that forms plasma from a process gas by supplying the process gas into a processing container and applying high-frequency power to an electrode provided inside the processing container on which a workpiece is placed and executes specific plasma processing on the processing surface of the workpiece, apparatus state parameter data indicating a state of the plasma processing apparatus are obtained through measurement executed by a parameter measuring instrument, optical data are obtained through measurement executed by an optical measuring instrument and electrical data are obtained through measurement executed by an electrical measuring instrument. A means for plasma leak judgment judges that a plasma leak has occurred if there is a fluctuation in the data.

12 Claims, 8 Drawing Sheets

PLASMA LEAK MONITORING METHOD, PLASMA PROCESSING APPARATUS AND PLASMA PROCESSING METHOD

BACKGROUND OF THE INVENTION

1. Field of the Invention

The present invention relates to a plasma monitoring method, a plasma processing apparatus and a plasma processing method, and more specifically, it relates to a plasma leak monitoring method, a plasma processing apparatus and a plasma processing method which make it possible to quickly detect a plasma leak occurring during a plasma processing.

2. Description of the Related Art

Semiconductors are manufactured by utilizing various types of manufacturing apparatuses and inspection apparatuses under diverse conditions. In particular, a plasma processing apparatus is sometimes utilized to execute processing by setting the pressure of the process gas inside the processing container to a relatively high level and also setting the high-frequency power that is applied to a high level so as to raise the density of the plasma being excited, as a way of enabling production of a semiconductor achieving higher integration and higher density.

When executing processing with such high density plasma, the plasma cannot be trapped at the top of the workpiece with a high degree of efficiency if a part such as an evacuation ring provided around the lower electrode which also functions as a workpiece stage is not mounted securely inside the plasma processing apparatus to result in a so-called plasma leak in which the plasma leaks out to another area such as a space under the evacuation ring. Since, in the event of a plasma leak, some workpieces may not be processed correctly even under processing conditions that are otherwise consistent, a problem arises in that the yield of the semiconductor production becomes poor.

Plasma processing apparatuses in the related art, which do not include a means for detection capable of detecting a plasma leak accurately, are not easily able to accurately determine whether not an abnormal workpiece processing state has been caused by a plasma leak and thus cannot correctly adjust the plasma processing apparatus state and the processing conditions.

An object of the present invention, which has been completed by addressing the problem of the plasma leak monitoring method and the plasma processing apparatuses in the related art, is to provide a new and improved plasma leak monitoring method, a new and improved plasma processing apparatus and a new and improved plasma processing method that make it possible to accurately and reliably detect a plasma leak.

SUMMARY OF THE INVENTION

In order to achieve the object described above, in a first aspect of the present invention, a plasma leak monitoring method for monitoring for plasma leakage in a plasma processing apparatus that executes a plasma processing on a workpiece by applying high-frequency power and thus generating plasma inside the airtight processing apparatus, characterized in that data indicating an apparatus state parameter related to the state of the plasma processing apparatus are obtained through measurement and a plasma leak occurring during the plasma processing is detected by monitoring the measurement data, is provided.

The apparatus state parameter mentioned above may be, for instance, a high-frequency voltage Vpp, the positions of variable capacitors C1 and C2 used to equalize the internal resistance on the source side and the resistance on the load side or the angle of the control valve at an automatic pressure control device (APC). It has been proven through repeated tests that when a plasma leak occurs, such apparatus state parameter data indicate a value different from the value indicated in a plasma leak-free state (the value deviates). Accordingly, the present invention enables speedy and reliable plasma leak detection by using the deviation occurring in the apparatus state parameter data to detect a plasma leak.

In addition, instead of the apparatus state parameter data described above, a plasma leak occurring during the plasma processing may be detected by detecting optical data indicating the intensity of light emitted from the plasma at a predetermined wavelength or electrical data related to the fundamental wave and the higher harmonic wave inherent to the plasma and then monitoring the detected data. It has been proven through repeated tests that when a plasma leak occurs, the optical data and the electrical data also indicate values different from those indicated in a plasma leak-free state. Thus, according to the present invention, a plasma leak can be detected speedily and reliably by detecting a plasma leak based upon a deviation of the value indicated by the optical data or the electrical data, as well.

Furthermore, a plasma leak occurring during plasma processing may be detected by using at least two types of data among the apparatus state parameter data, the optical data and the electrical data in combination. Since the value indicated by a given type of data may fluctuate greatly due to an abnormality other than a plasma leak, a judgment that a plasma leak has occurred can be made with an even higher degree of accuracy by combining at least two types of data.

In order to achieve the object described above, in a second aspect of the present invention, a plasma processing apparatus that executes a specific type of plasma processing on a processing surface of a workpiece by applying high-frequency power to an electrode, provided within a processing container, on which the workpiece is placed, while supplying a process gas into the processing container, thereby generating plasma with the process gas, comprising a means for measurement that obtains through measurement apparatus state parameter data related to a state of the plasma processing apparatus and a means for detection that detects an occurrence of a plasma leak during the plasma processing based upon the measured apparatus state parameter, is provided. The monitoring method described earlier is realized in such a plasma processing apparatus.

Alternatively, the plasma processing apparatus may comprise a means for measurement that obtains through measurement either optical data indicating the intensity of light emitted from the plasma at a predetermined wavelength or electrical data related to the fundamental wave and the higher harmonic wave inherent to the plasma and a means for detection that detects an occurrence of a plasma leak during the plasma processing by using either type of data.

As a further alternative, the plasma processing apparatus may comprise a means for measurement that obtains through measurement at least two types of data among the apparatus state parameter data, the optical data and the electrical data and a means for detection that detects a plasma leak occurring during the plasma processing by using the measurement data. This structure enables reliable detection of a plasma leak and ultimately improves the yield of the plasma process.

In order to achieve the object described above, in a third aspect of the present invention, a plasma processing method for executing plasma processing on a workpiece by applying high-frequency power thereby generating plasma inside the airtight processing apparatus, characterized in that a plasma leak occurring during the plasma processing is detected by obtaining through measurement apparatus state parameter data related to a state of the plasma processing apparatus and monitoring the measurement data, is provided. Since a plasma leak can be detected during plasma processing by adopting this method, workpieces can be processed with the plasma in a desirable manner to lower the yield of the semiconductor production.

Alternatively, optical data indicating the intensity of light emitted from the plasma at a predetermined wavelength or electrical data related to the fundamental wave and the higher harmonic wave inherent to the plasma may be detected instead of the apparatus state parameter and a plasma leak occurring during the plasma processing may be detected by monitoring the detected data in the plasma processing method. A plasma leak can be detected during the plasma processing in this manner as well to allow the workpieces to be processed correctly.

Furthermore, a plasma leak occurring during the plasma processing may be detected by using at least two types of data among the apparatus state parameter data, the optical data and the electrical data in combination. Since a judgment that a plasma leak has occurred can be made with an even higher degree of accuracy by combining at least two different types of data, the workpieces can be correctly processed with the plasma even more reliably.

In the plasma leak detection, a judgment that a plasma leak has occurred may be made based upon a fluctuation manifesting in the measurement data. In more specific terms, if there is a fluctuation whereby a value indicated by the data exceeds a preset value, for instance, it may be judged that a plasma leak has occurred.

DETAILED DESCRIPTION OF THE PREFERRED EMBODIMENT

Figure 1:
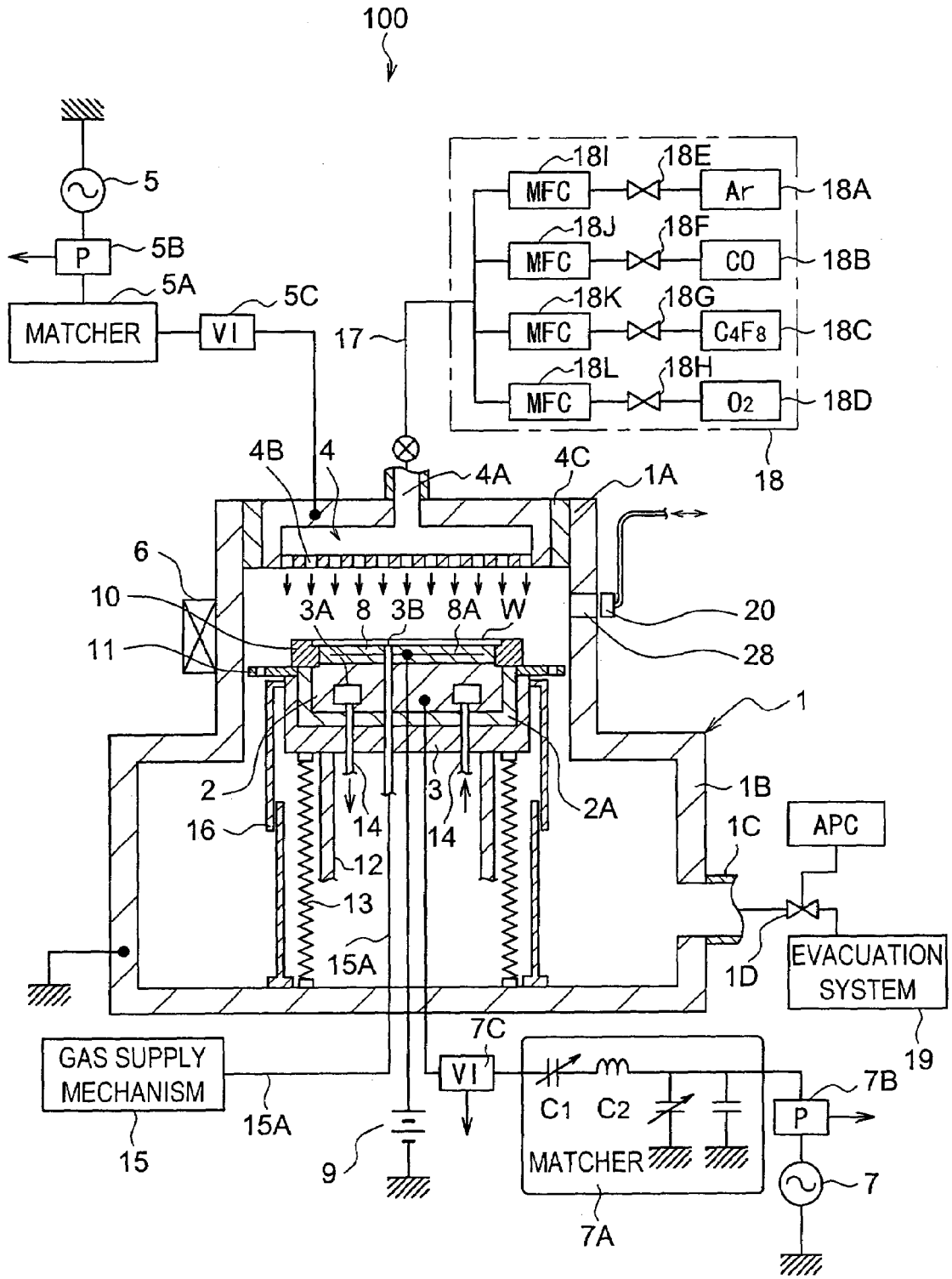
FIG. 1 is a schematic a sectional view of the plasma processing apparatus achieved in an embodiment of the present invention.

The following is a detailed explanation of a preferred embodiment of the plasma leak monitoring method and a plasma processing apparatus according to the present invention, given in reference to the attached drawings. It is to be noted that in the specification and the drawings, the same reference numerals are assigned to components having substantially identical functions and structural features to preclude the necessity for a repeated explanation thereof.

FIG. 1 is a schematic sectional view illustrating the structure of a plane parallel plasma etching apparatus constituting a plasma processing apparatus 100 achieved in an embodiment of the present invention. As shown in FIG. 1, the plasma processing apparatus 100 includes a processing chamber 1 constituted of aluminum, an aluminum supporting body 3 capable of moving up and down, which supports a lower electrode 2 provided inside the processing chamber 1 via an insulating member 2A and a shower head (may also be referred to as an upper electrode) provided above the supporting body 3, which is used to supply a process gas and is also used as an upper electrode.

An insulator 4C is provided between the shower head 4 and the processing chamber 1 to electrically insulate the shower head 4 and the processing chamber 1 from each other. In addition, a first high-frequency source 5 is connected to the shower head 4 via a matcher 5A, and first high-frequency power having a frequency equal to or higher than 30 MHz and more desirably, a frequency of 60 MHz is supplied to the shower head 4 from the first high-frequency source 5. The first high-frequency power P is measured via a power meter 5B connected between the high-frequency source 5 and the matcher 5A.

The upper part of the processing chamber 1 forms an upper chamber 1A having a small diameter, whereas the lower part of the processing chamber 1 forms a lower chamber 1B having a larger diameter. An access port through which a wafer W is carried in and out is formed at the upper chamber 1A, with a gate valve 6 mounted at the access port. In addition, a second high-frequency source 7 is connected to the lower electrode 2 via a matcher 7A, and second high-frequency power P with a 13.56 MHz frequency is applied from the second high-frequency source 7 to the lower electrode 2 to form an electric field along the vertical direction between the shower head 4 and the lower electrode 2. The second high-frequency power P is measured via a power meter 7B connected between the second high-frequency source 7 and the matcher 7A.

In addition, electrical measuring instruments (e.g., VI probes) 5C and 7C are mounted at the matchers 5A and 7A at positions toward the electrodes 4 and 2 respectively, and a high-frequency voltage V, a high-frequency current I and an impedance Z of the fundamental wave and the higher harmonic wave inherent to the plasma generated inside the upper chamber 1A with the high-frequency power P applied to the electrodes 4 and 2 are measured via the electrical measuring instruments 5C and 7C. The high frequency voltage V and high-frequency current I, together with the high-frequency power P and the impedance Z, are used as electrical data to detect a plasma leak. These electrical parameters may be detected through both electrical measuring instruments 5C and 7C, or they may be detected through either one of them.

The matchers 5A and 7A are each internally provided with, for instance, two variable capacitors C1 and C2, a capacitor C and a coil L and achieve impedance matching via the variable capacitors C1 and C2. More specifically, the values (positions) representing the positions of the variable capacitors at which the internal resistance on the source side (the cable side) and the resistance on the load side (on the processing chamber side) are equalized to each other are detected as the detection values of the variable capacitors C1 and C2. The positions of the variable capacitors C1 and C2 in a matched state, and a high-frequency voltage Vpp measured by measuring instruments (not shown) inside the matchers 5A and 7A, together with the degree of opening of a control valve (the APC angle) of an auto pressure controller (APC) that is to be detailed later and the like, constitute parameters that are to be referred to as apparatus state parameters hereafter. The apparatus state parameters, too, are used to detect a plasma leak.

An electrostatic chuck 8 is provided at the upper surface of the lower electrode 2, with a DC source 9 connected to an electrode plate 8A of the electrostatic chuck 8. Thus, as a high voltage from the DC source 9 is applied to the electrode plate 8A in a strong vacuum, the wafer W becomes electrostatically held onto the electrostatic chuck 8. A focus ring 10 is provided at the outer circumference of the lower electrode 2 to direct the plasma generated inside the upper chamber 1A to the vicinity of the wafer W. In addition, an evacuation ring 11 is mounted at the top of the supporting body 3 under the focus ring 10. A plurality of holes are formed at the evacuation ring 11 with equal intervals along the circumferential direction over the entire circumference of the evacuation ring 11, and the gas inside the upper chamber 1A is evacuated into the lower chamber 1B through these holes.

The supporting body 3 is allowed to move up and down between the upper chamber 1A and the lower chamber 1B via a ball screw mechanism 12 and a bellows 13. Thus, the distance between the lower electrode 2 and the shower head 4 can be set to a specific value.

Coolant flow passages 3A which are connected to coolant pipings 14 are formed inside the supporting body 3 so that the coolant is circulated inside the coolant flow passages 3A via the coolant pipings 14 to adjust the temperature of the wafer W at a specific level. In addition, a gas flow passage 3B is formed at the supporting body 3, the insulating member 2A, the lower electrode 2 and the electrostatic chuck 8 so that He gas achieving a specific pressure level is supplied as a back side gas into the narrow gap between the electrostatic chuck 8 and the wafer W via a gas piping 15A from a gas supply mechanism 15 to promote heat conduction between the electrostatic chuck 8 and the wafer W via the He gas. It is to be noted that a bellows cover 16 is provided under the evacuation ring 11.

At the upper surface of the shower head 4, a gas supply port 4A is formed, and a process gas supply system 18 is connected to the gas supply port 4A via a piping 17. The process gas supply system 18 includes an Ar gas supply source 18A, a CO gas supply source 18B, a $C_5F_8$ gas supply source 18C and an $O_2$ gas supply source 18D. The individual gases are supplied at predetermined flow rate settings via valves 18E, 18F, 18G and 18H and mass flow controllers 18I, 18J, 18K and 18L from these gas supply sources 18A, 18B, 18C and 18D respectively, and they are then adjusted inside the shower head 4 to form a mixed gas achieving a predetermined mixing ratio. The flow rates of the individual gases can be detected at the respective mass flow controllers 18I, 18J, 18K and 18L.

A plurality of holes 4B are disposed uniformly over the entire lower surface of the shower head 4 so as to supply the mixed gas to be used as the process gas into the upper chamber 1A from the shower head 4 via the holes 4B. In addition, an evacuation pipe 1C is connected to an evacuation hole located toward the bottom of the lower chamber 1B, and a predetermined gas pressure level is maintained inside the processing chamber 1 by evacuating the processing chamber 1 via an evacuation system 19 constituted of a vacuum pump and the like, which is connected to the evacuation pipe 1C. An APC valve 1D is provided at evacuation pipe 1C and the degree of its opening is automatically adjusted in correspondence to the gas pressure inside the processing chamber 1. This degree of opening (hereafter to be referred to as an APC angle) constitutes an apparatus state parameter indicating an apparatus state, as explained earlier, which is a parameter that cannot be controlled. While apparatus state parameters constituted of a plurality of types of apparatus state data including the data indicating the APC angle mentioned above are used in the embodiment, apparatus state data constituted of one type of apparatus state parameter among these apparatus state parameters may be used instead.

A detection window 28 used to detect light emitted inside the processing chamber 1 is provided at a side wall of the upper chamber 1A, and a spectrometer (hereafter referred to as an optical measuring instrument) 20 that detects plasma light emission inside the processing chamber 1 is provided directly outside the detection window 28. The state of the plasma is monitored based upon optical data related to a specific wavelength that are obtained at the optical measuring instrument 20 to detect the end point of the plasma process. These optical data, too, are used for plasma leak detection.

Figure 2:
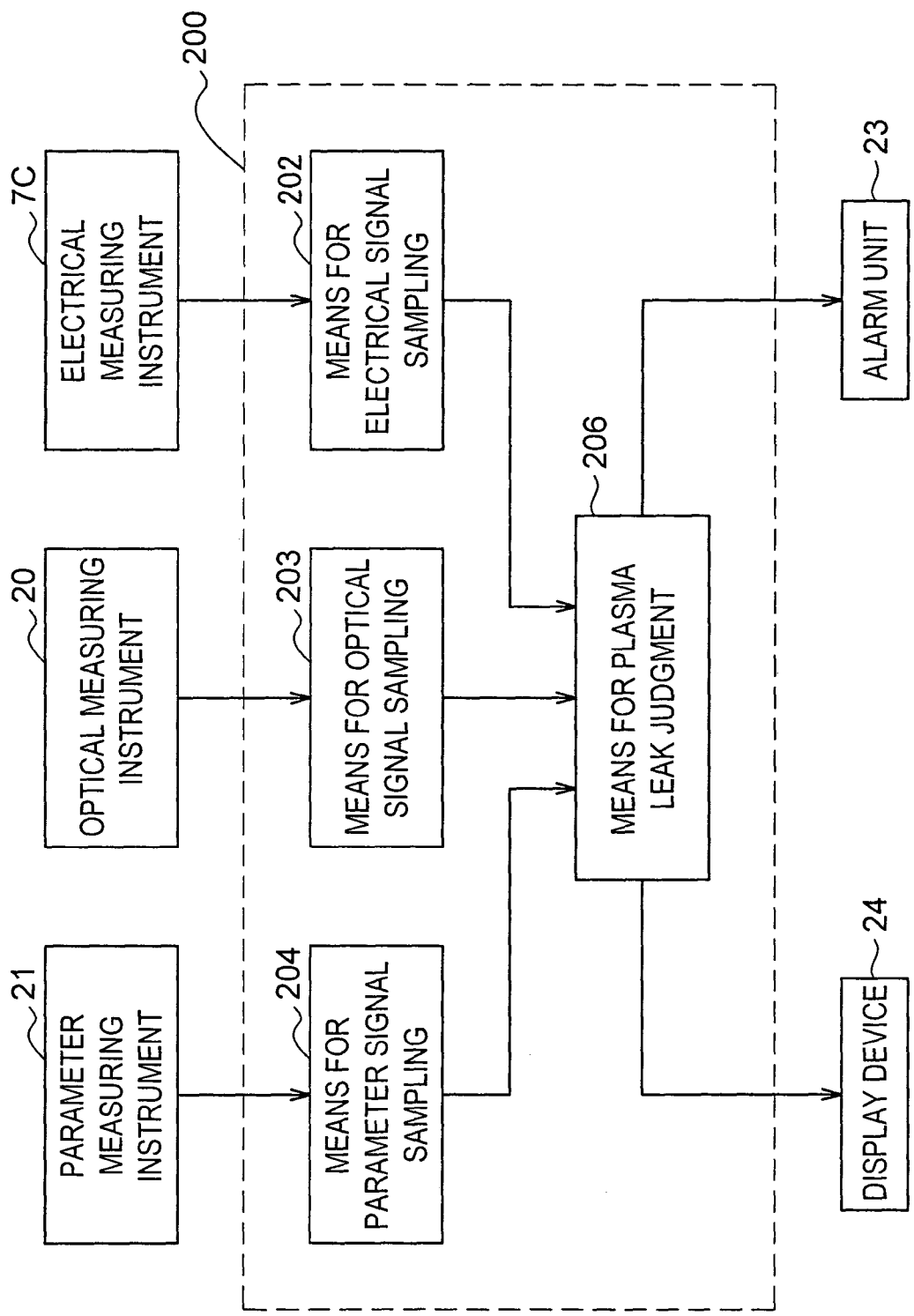
FIG. 2 is a block diagram showing an example of the means for plasma leak judgment utilized in the embodiment.

FIG. 2 is a block diagram showing a structural example that may be adopted in a means for plasma leak detection 200 in the plasma processing apparatus 100. As shown in FIG. 2, the plasma processing apparatus 100 includes the means for plasma leak detection 200. The means for plasma leak detection 200 may comprise, for instance, a means for electrical signal sampling 202, a means for optical signal sampling 203 and a means for parameter signal sampling 204 that intermittently sample signals provided by the electrical measuring instrument 7C which obtains the electrical data through measurement, the optical measuring instrument 20 which obtains the optical data through measurement and a parameter measuring instrument 21 which obtains the apparatus state parameters through measurement respectively, and a means for plasma leak judgment 206 that makes a judgment as to whether or not a plasma leak has occurred by using the various types of sampled data.

In addition, an alarm unit 23 and a display device 24 are connected to the means for plasma leak detection 200. The alarm unit 23 and the display device 24 are utilized to alert the operating personnel to an abnormal state in the event that the means for plasma leak judgment 206 verifies that a plasma leak has occurred.

Figure 3A:
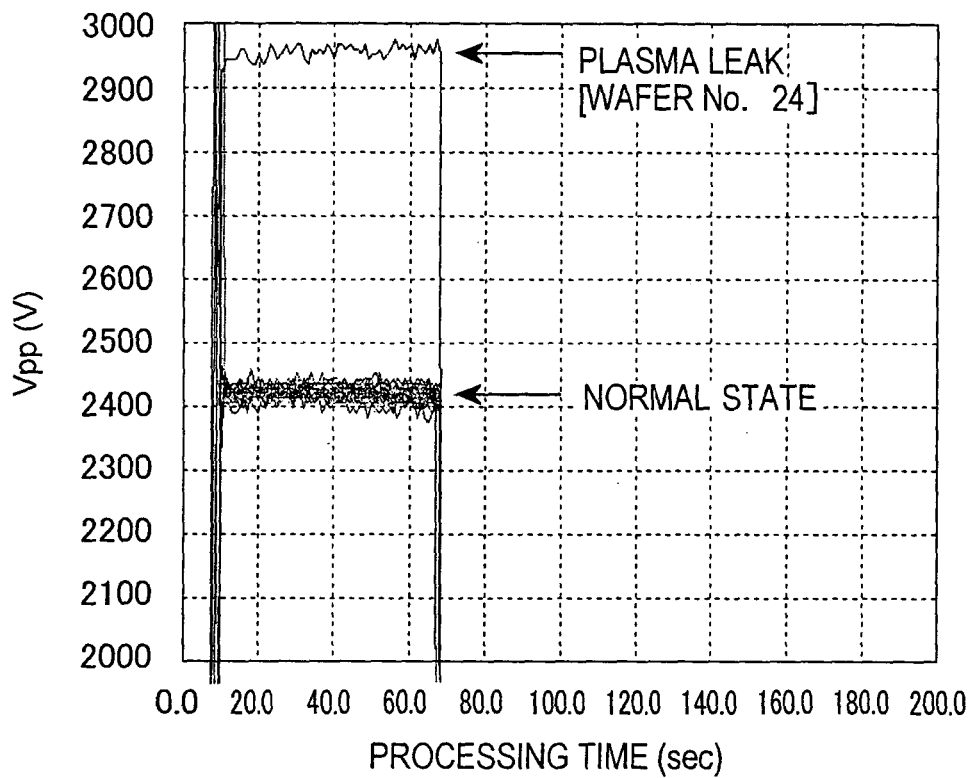
FIG. 3 presents examples of the apparatus state parameter measurement executed in the embodiment.
Figure 3B:
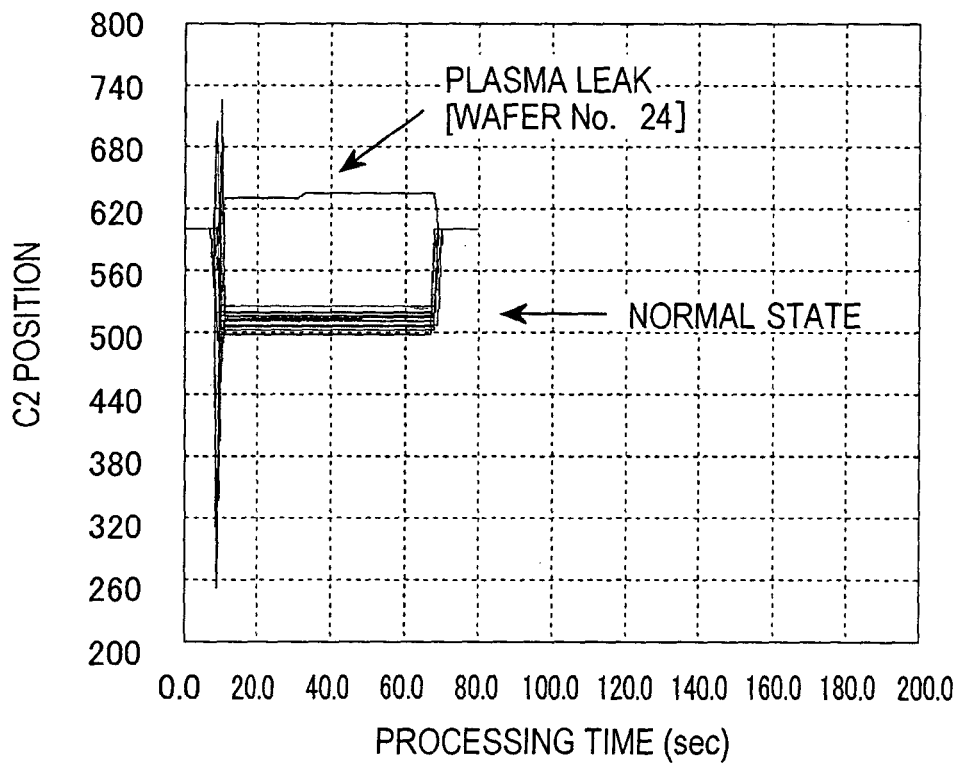
Figure 4A:
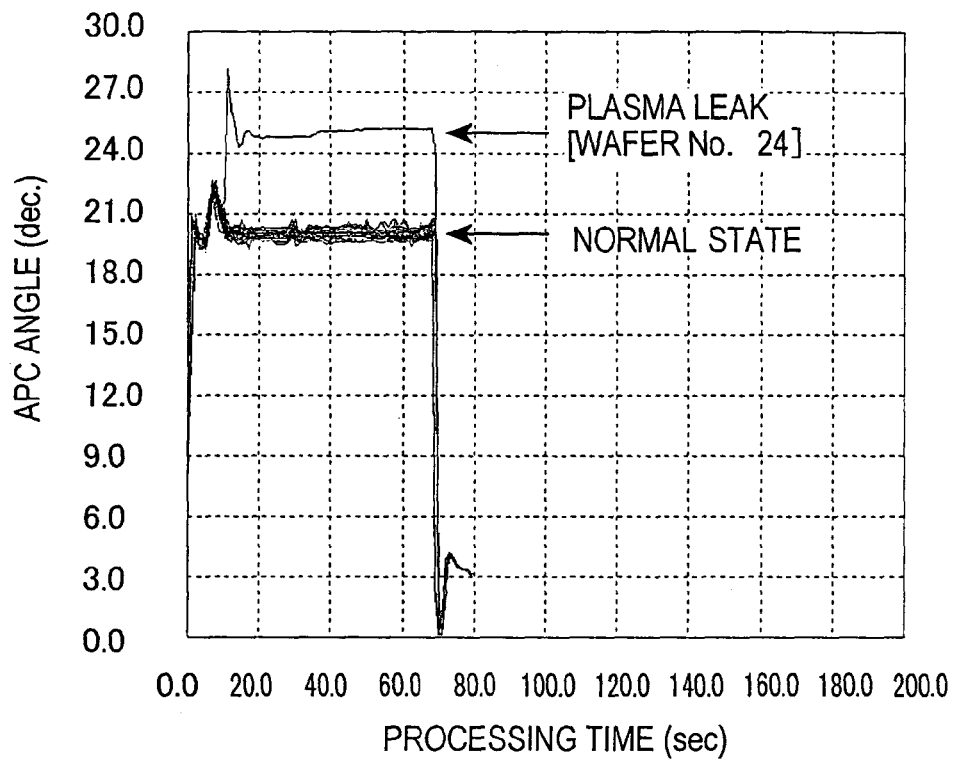
FIG. 4 presents examples of the apparatus state parameter measurement executed in the embodiment.
Figure 4B:
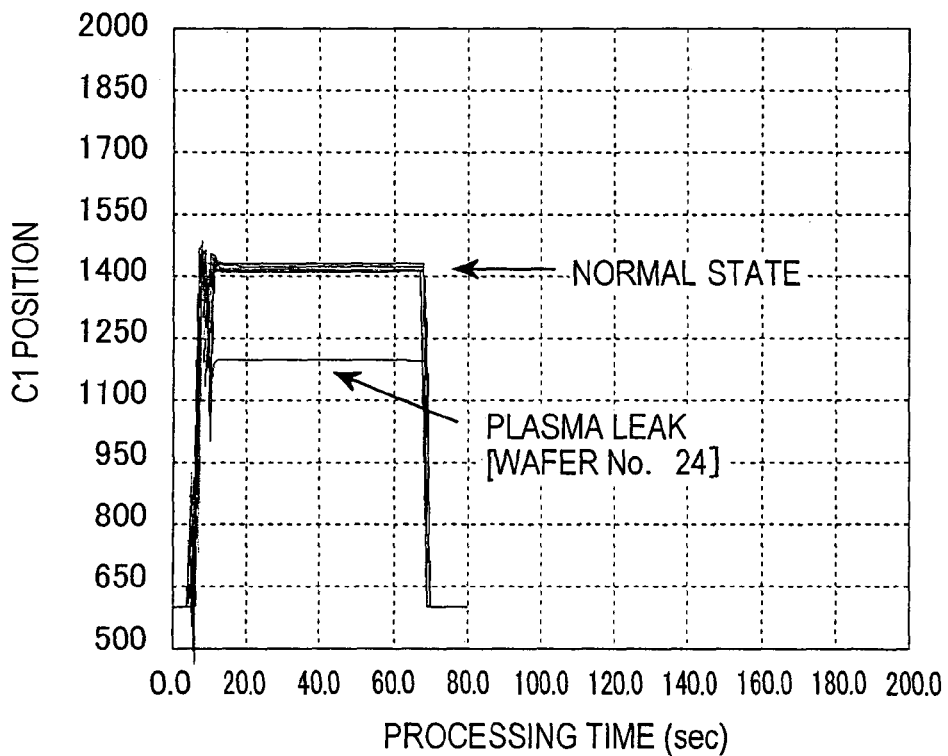

Next, an instance of detecting a plasma leak by using the apparatus state parameters is explained. FIGS. 3 and 4 present examples of the apparatus state parameter measurement. FIGS. 3A, 3B, 4A and 4B respectively indicate the high-frequency voltage Vpp, which is one of the apparatus state parameters, the C2 position value corresponding to the variable capacitor C2, the APC angle and the C1 position value corresponding to the variable capacitor C1. In these figures, the length of the processing time is indicated along the horizontal axis, and the values obtained by processing 25 wafers, i.e., wafers Nos. 1 through 25, are superimposed on one another. The etching process was executed under conditions that include; the pressure inside the processing container 1 set to 25 mTorr, the level of the high-frequency power applied to the shower head 4 set to 3300 W, the level of the high-frequency power applied to the lower electrode 2 set to 3800 W, the flow rates of the constituents of the process gas set to $C_5F_8/Ar/O_2=29/750/47$ sccm, the temperatures of the shower head 4 and the side wall of the processing container 1 both set to 60° C. and the temperature of the lower electrode 2 set to 20° C. During the etching process executed under these etching process conditions, a plasma leak occurred while processing the 24th wafer. Now, the individual parameter values are examined.

As FIGS. 3 and 4 indicate, the values indicating the high-frequency voltage Vpp, the C2 position and the APC angle that were obtained while processing of the 24th wafer are clearly higher than the corresponding values obtained while processing the other 24 wafers, whereas the value indicating the C1 position, which was obtained while processing the 24th wafer is clearly lower than the corresponding values obtained while processing the other 24 wafers. This means that a decision that a plasma leak has occurred can be made if the values indicating the high-frequency voltage Vpp, the capacitor C1 position, the capacitor C2 position and the APC angle which are measured as various types of apparatus state data constituting the apparatus state parameters are clearly different from the values obtained while processing other wafers.

More specifically, the means for plasma leak judgment 206 may be preprogrammed to judge that a plasma leak has occurred and engage the display device 24 and the alarm unit 23 to alert the operating personnel if a fluctuation beyond a range of ±2 σ with σ representing a standard deviation set for a given measurement value is detected. During the judgment process, an abnormal state may be judged to have occurred if any one of the measurement values indicating the high-frequency voltage Vpp, the capacitor C1 position, the capacitor C2 position and the APC angle has deviated beyond the predetermined range explained above, or it may be judged the an abnormality has occurred if, for instance, any two or more of the measurement values have deviated beyond their respective predetermined ranges, instead.

Figure 5A:
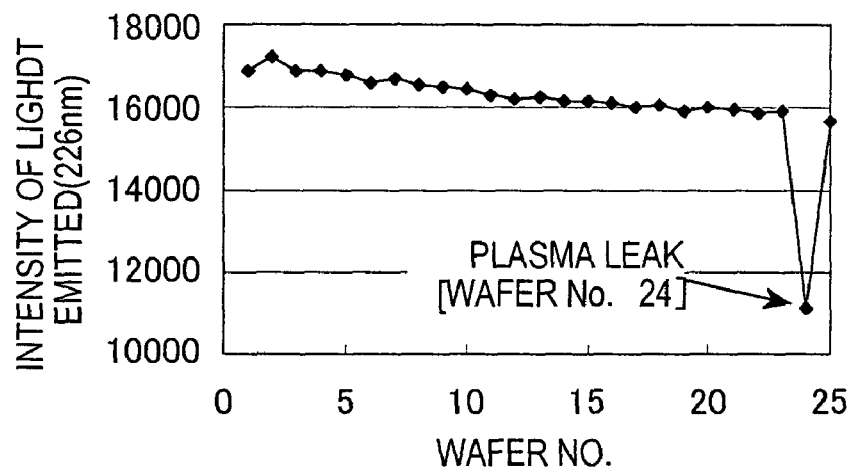
FIG. 5 presents examples of optical data measurement executed in the embodiment.
Figure 5B:
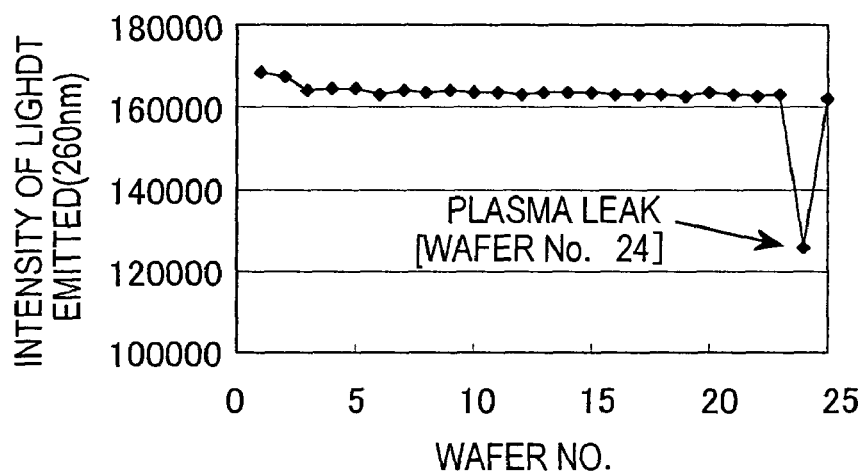
Figure 5C:
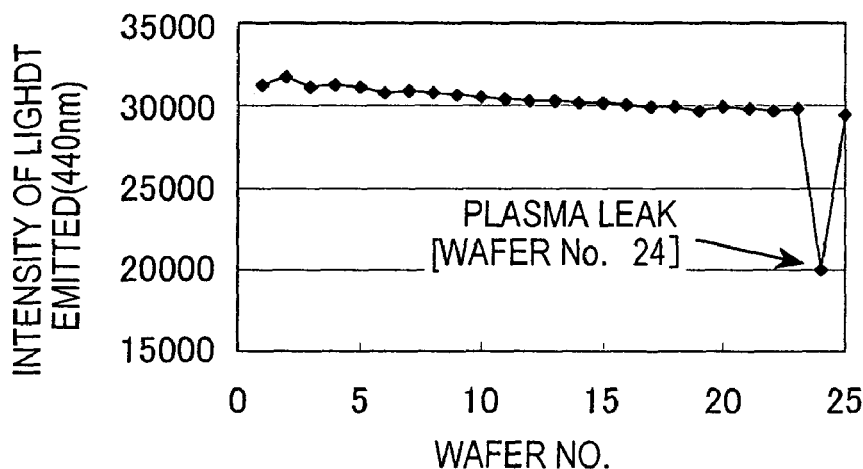

Next, an instance of detecting a plasma leak by using the optical data is explained. FIG. 5 present examples of the optical data measurement. FIG. 5A, FIG. 5B and FIG. 5C indicate the intensity of light emitted from the plasma generated inside the processing container, measured at wavelengths of 226 nm, 260 nm and 440 nm respectively. The wafer numbers are indicated along the horizontal axis. The etching process was executed under conditions that include; the pressure inside the processing container 1 set to 25 mTorr, the level of the high-frequency power applied to the shower head 4 set to 3300 W, the level of the high-frequency power applied to the lower electrode 2 set to 3800 W, the flow rates of the constituents of the process gas set to $C_5F_8/Ar/O_2=29/750/47$ sccm, the temperatures of the shower head 4 and the side wall of the processing container 1 both set to 60° C. and the temperature of the lower electrode 2 set to 20° C. During the etching process executed under these etching process conditions, a plasma leak occurred while processing the 24th wafer. Now, the individual parameter values are examined.

The values indicated in FIG. 5 which were obtained while processing the 24th wafer are clearly lower than the values obtained while processing the other 24 wafers at all the wavelengths. This means that if a value indicated by optical data obtained through measurement while processing a given wafer is clearly different from the values obtained while processing other wafers, it can be judged that a plasma leak has occurred.

Figure 6:
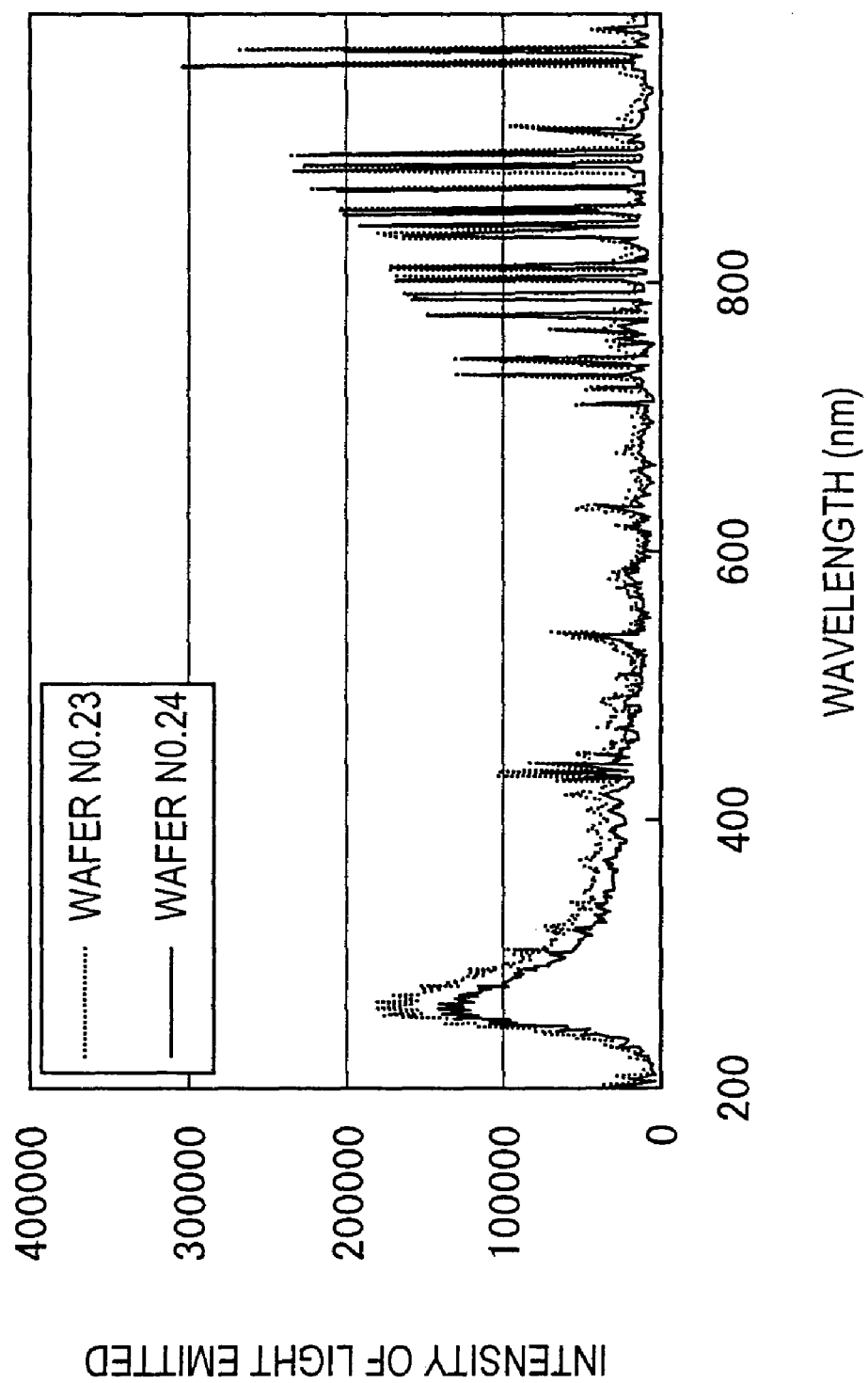
FIG. 6 summarizes the results of the optical data measurement obtained at varying wavelengths in the embodiment.
Figure 7A:
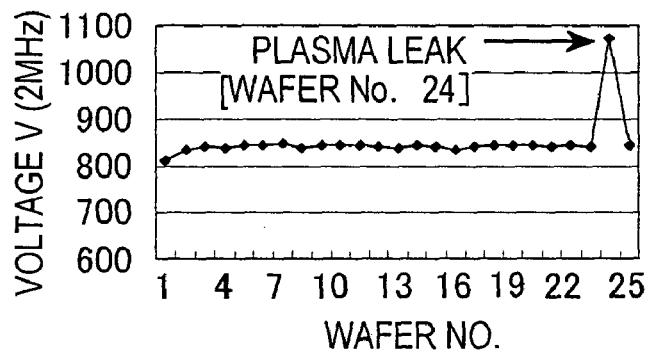
FIG. 7 presents examples of electrical data measurement executed in the embodiment.
Figure 7B:
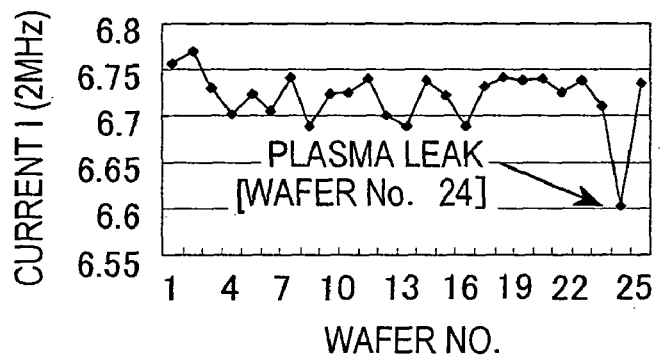
Figure 7C:
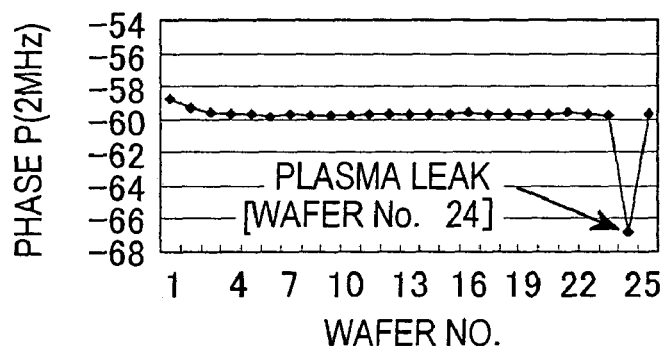
Figure 7D:
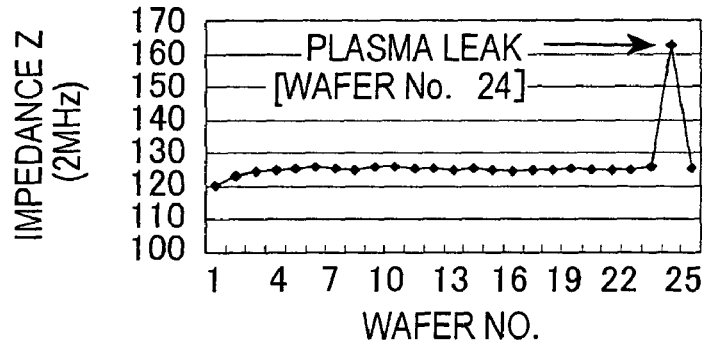

More specifically, the means for plasma leak judgment 206 may be preprogrammed to judge that a plasma leak has occurred and engage the display device 24 and the alarm unit 23 to alert the operating personnel if a fluctuation beyond a range of ±2 σ with σ representing a standard deviation set for a given measurement value is detected. During this judgment process, an abnormal state may be judged to have manifested if the measurement value at any of the various wavelengths has deviated beyond the predetermined range, or it may be judged that an abnormality has occurred if two or more measurement values have deviated beyond the corresponding predetermined ranges. It is to be noted that FIG. 6 presents the optical data of the 23rd wafer and the optical data of the 24th wafer measured at various wavelengths, in comparison to each other, with the vertical axis indicating the light emission intensity and the horizontal axis indicating the wavelength. FIG. 6 indicates that there is a deviation in the intensity level of the light emission between the 23rd wafer and the 24th wafer at the various wavelengths. This deviation in the light emission intensity is particularly noticeable over a wavelength range of approximately 200 nm~700 nm.

Next, an instance of detecting a plasma leak by using the electrical data is explained. FIG. 7 presents examples of optical data measurement. FIG. 7A, FIG. 7B, FIG. 7C and FIG. 7D respectively indicate the voltage V, the current I, the phase P and the impedance Z, all measured with regard to a 2 MHz higher harmonic wave component the wafer numbers are indicated along the horizontal axis the etching process was executed under conditions that include; the pressure inside the processing container 1 set to 25 mTorr, the level of the high-frequency power applied to the shower head 4 set to 3300 W, the level of the high-frequency power applied to the lower electrode 2 set to 3800 W, the flow rates of the constituents of the process gas set to $C_5F_8/Ar/O_2=29/750/47$ sccm, the temperatures of the shower head 4 and the side wall of the processing container 1 both set to 60° C. and the temperature of the lower electrode 2 set to 20° C. During the etching process executed under these etching process conditions, a plasma leak occurred while processing the 24th wafer. Now, the individual parameter values are examined.

In FIG. 7, the values indicating the voltage V and the impedance Z which were measured while processing the 24th wafer are clearly higher than the corresponding values measured while processing the other 24 wafers, whereas the values indicating the current I and the phase P which were measured while processing the 24th wafer are clearly lower than the corresponding values measured while processing the other 24 wafers. This means that if a value indicated by electrical data which are obtained through measurement while processing a given wafer is clearly different from the values measured while processing other wafers, it can be judged that a plasma leak has occurred.

It has been confirmed that with regard to the electrical data, the data fluctuate along the directions indicated in Table 1 below when a plasma leak has occurred over the entire range of higher harmonic wave components.

TABLE 1

|  | 2 MHz | 4 MHz | 6 MHz | 8 MHz | 10 MHz | 12 MHz | 14 MHz | 20 MHz | 40 MHz |
| --- | --- | --- | --- | --- | --- | --- | --- | --- | --- |
| voltage V | higher | higher | higher |  | higher | higher | higher | higher | lower |
| current I | lower |  | lower | higher | higher | higher | higher | lower | lower |
| phase P | lower |  | lower | higher | lower | lower | higher | higher | higher |
| impedance Z | higher | higher | higher | lower | lower | lower | lower | higher | higher |

Accordingly, the means for plasma leak judgment 206 may be preprogrammed to judge that a plasma leak has occurred and engage the display device 24 and the alarm unit 23 to alert the operating personnel if a fluctuation beyond a range of ±2 σ with σ representing a standard deviation set for a given measurement value is detected along the fluctuation direction for the corresponding data. During the judgment process, an abnormal state may be judged to have occurred if any one of the measurement values indicating the voltage V, the current I, the phase P and the impedance Z has deviated beyond the predetermined range explained above, or it may be judged that an abnormality has occurred if, for instance, any two or more of the measurement values have deviated beyond their respective predetermined ranges, instead.

Figure 8A:
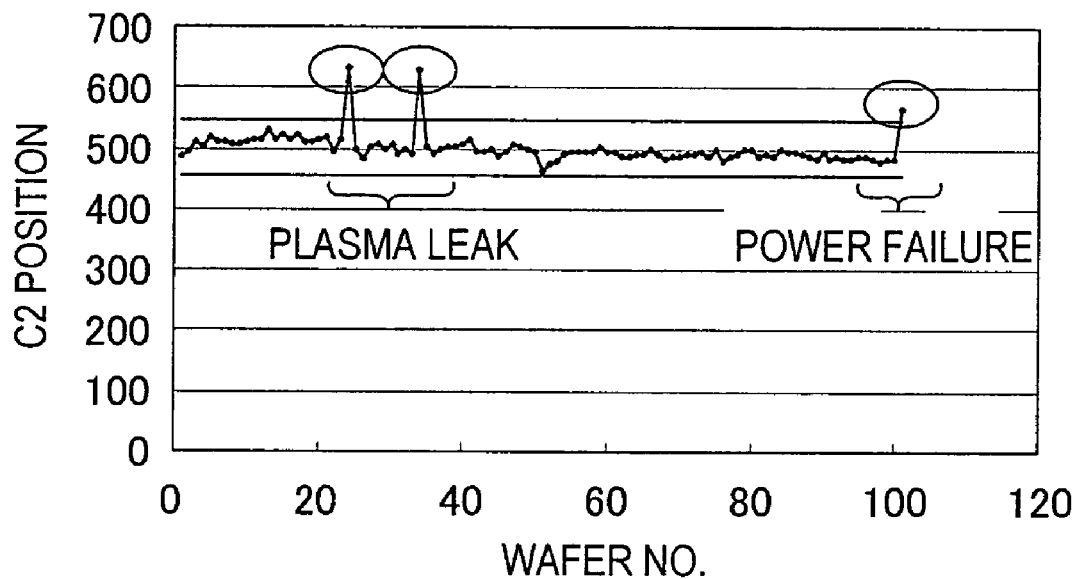
FIG. 8 shows how different types of data may be used in combination in the plasma leak judgment method in the embodiment.
Figure 8B:
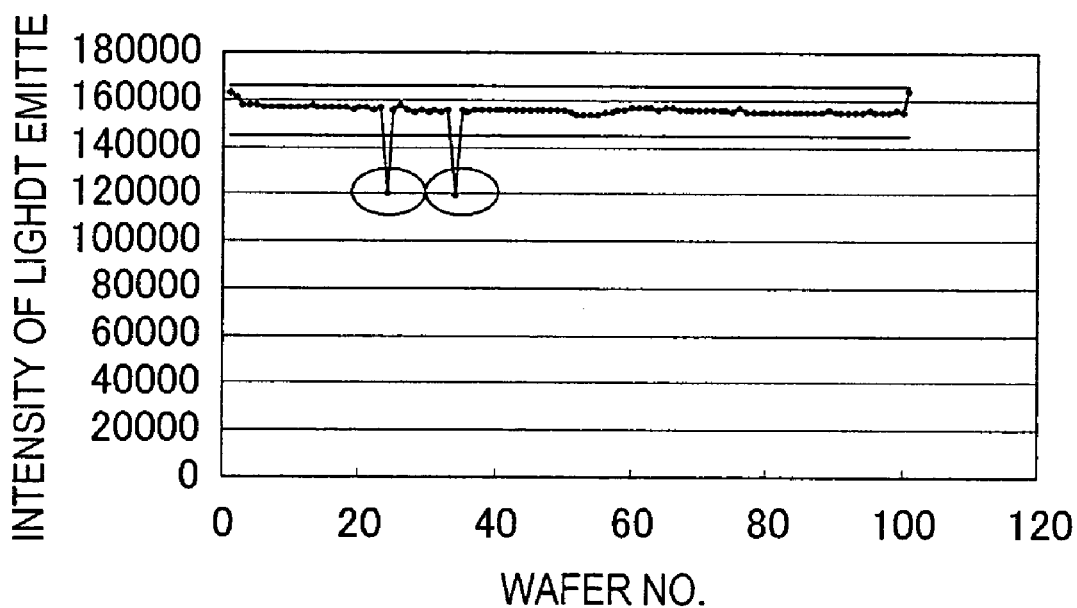

Next, an example, in which a judgment that a plasma leak has occurred is made by using a combination of at least two types of measurement results among the apparatus state parameter data, the optical data and the electrical data described above is explained. FIG. 8 illustrates a method that may be adopted in a plasma leak judgment when using different types of data in combination. FIG. 8A indicates the capacitor C2 position which is one of the apparatus state parameters and FIG. 8B indicates the intensity of the light emission at 260 nm in the optical data, with the optical axis in both figures indicating the wafer number.

As shown in FIG. 8A, the value indicating the capacitor C2 position fluctuates significantly in the vicinity of wafer Nos. 25, 35 and 100. While the light emission intensity, too, fluctuates in the vicinity of wafer Nos. 25, 35 and 100, the fluctuation occurring in the vicinity of wafer No. 100 is clearly smaller than the other fluctuations, and, for this reason, it is not judged that a plasma leak has occurred while processing wafer No. 100. It is to be noted that the other data substantiate the fact that this fluctuation is attributable to a fluctuation in the high-frequency power that is applied. Since a large fluctuation may occur in the measurement value indicated by a given type of data due to an abnormality other than a plasma leak, as described above, two or more types of data are used in combination to make an even more accurate judgment with regard to a plasma leak.

More specifically, the means for plasma leak judgment 206 may be preprogrammed to judge that a plasma leak has occurred and engage the display device 24 and the alarm unit 23 to alert the operating personnel if fluctuations beyond a range of ±2 σ with σ representing a standard deviation set for the individual measurement values are detected. By using at least two types of data obtained through measurement among the apparatus state parameter data, the optical data and the electrical data, in particular, the risk of erroneously judging that a plasma leak has occurred based upon a fluctuation in a measurement value attributable to another cause is eliminated and thus, an accurate plasma leak detection is enabled.

While the invention has been particularly shown and described with respect to a preferred embodiment of the plasma leak monitoring method and the plasma processing apparatus according to the present invention by referring to the attached drawings, the present invention is not limited to this example and it will be understood by those skilled in the art that various changes in form and detail may be made therein without departing from the spirit, scope and teaching of the invention.

For instance, the present invention may be adopted in a plasma processing apparatus other than a plane parallel plasma etching apparatus, and it may be adopted in a helicon wave plasma etching apparatus, an inductively coupled plasma etching apparatus and the like that generate plasma inside a processing chamber. In addition, the present invention may be adopted in an etching apparatus that generates plasma by using a dipole ring magnet. Alternatively, it may be adopted in a plasma etching apparatus that applies high-frequency power to the lower electrode alone.

As explained above, the present invention enables an accurate judgment with regard to a plasma leak by monitoring apparatus state parameters, optical data and electrical data, which fluctuate in the event of a plasma leak, and thus allows the processing in the plasma processing apparatus to be executed in a stable manner.

What is claimed is:

1. A plasma leak monitoring method for monitoring a plasma processing apparatus that executes plasma processing on a workpiece with plasma generated inside an airtight processing apparatus by applying high-frequency power, wherein:

measurement data constituted of apparatus state parameter data related to a state of said plasma processing apparatus, are obtained through measurement and a plasma leak occurring during the plasma processing is detected by monitoring said measurement data.

2. A plasma leak monitoring method for monitoring a plasma processing apparatus that executes a plasma processing on a workpiece with plasma generated inside an airtight processing apparatus by applying high-frequency power, wherein:

measurement data constituted of either optical data indicating the intensity of light emitted from the plasma at a predetermined wavelength or electrical data related to a fundamental wave and a higher harmonic wave inherent to the plasma are obtained through measurement and a plasma leak occurring during the plasma processing is detected by monitoring said measurement data.

3. A plasma leak monitoring method for monitoring a plasma processing apparatus that executes a plasma processing on a workpiece with plasma generated inside an airtight processing apparatus by applying high-frequency power, wherein:

at least two types of measurement data among apparatus state parameter data indicating a state of the plasma processing apparatus, optical date indicating the intensity of light emitted from the plasma at a predetermined wavelength and electrical data related to a fundamental wave and a higher harmonic wave attributable to the plasma are obtained through measurement and a plasma leak occurring during the plasma processing is detected by a monitoring said measurement data.

4. A plasma leak monitoring method according to claim 1, wherein:

during the plasma leak detection, a plasma leak is judged to have occurred based upon a fluctuation in said measurement data.

5. A plasma processing apparatus that executes a plasma processing on a workpiece with plasma generated inside an airtight processing apparatus by applying high-frequency power, comprising:

a means for measurement that obtains measurement data constituted of apparatus state parameter data indicating a state of the plasma processing apparatus through measurement; and a means for detection that detects a plasma leak during the plasma processing by monitoring said measurement data.

6. A plasma processing apparatus that executes a plasma processing on a workpiece with plasma generated inside an airtight processing apparatus by applying high-frequency power, comprising:
- a means for measurement that obtains measurement data constituted of either optical data indicating the intensity of light emitted from the plasma at a predetermined wavelength or electrical data related to a fundamental wave or a higher harmonic wave inherent to the plasma through measurement; and
- a means for detection that detects a plasma leak during the plasma processing by monitoring said measurement data.

7. A plasma processing apparatus that executes a plasma processing on a workpiece with plasma generated inside an airtight processing apparatus by applying high-frequency power, comprising:
- a means for measurement that obtains at least two types of measurement data among apparatus state parameter data indicating a state of the plasma processing apparatus, optical data indicating the intensity of light emitted from the plasma at a predetermined wavelength and electrical data related to a fundamental wave and a higher harmonic wave attributable to the plasma through measurement; and
- a means for detection that detects a plasma leak during the plasma processing by monitoring said measurement data.

8. A plasma processing apparatus according to claim 5, wherein:
- during the plasma leak detection, a plasma leak is judged to have occurred based upon a fluctuation in said measurement data.

9. A plasma processing method for executing plasma processing on a workpiece with plasma generated inside an airtight processing apparatus by applying high-frequency power, wherein:
- during said plasma process, measurement data constituted of apparatus state parameter data indicating a state of the plasma processing apparatus are obtained through measurement and a plasma leak occurring during the plasma processing is detected by monitoring said measurement data.

10. A plasma processing method for executing plasma processing on a workpiece with plasma generated inside an airtight processing apparatus by applying high-frequency power, wherein:
- during said plasma process, measurement data constituted of either optical data indicating the intensity of light emitted from the plasma at a predetermined wavelength or electrical data related to a fundamental wave and a higher harmonic wave attributable to the plasma are obtained through measurement, and a plasma leak occurring during the plasma processing is detected by monitoring said measurement data.

11. A plasma processing method for executing plasma processing on a workpiece with plasma generated inside an airtight processing apparatus by applying high-frequency power, wherein:
- during said plasma process, measurement data constituted of at least two types of data among apparatus state parameter data indicating a state of the plasma processing apparatus, optical data indicating the intensity of light emitted from the plasma at a predetermined wavelength and electrical data related to a fundamental wave and a higher harmonic wave inherent to the plasma are obtained through measurement and a plasma leak occurring during the plasma processing is detected by monitoring said measurement data.

12. A plasma processing method according to claim 9, wherein:
- during the plasma leak detection, a plasma leak is judged to have occurred based upon a fluctuation in said measurement data.

\* \* \* \* \*